(12) United States Patent
Lei et al.

(10) Patent No.: US 11,458,105 B2
(45) Date of Patent: *Oct. 4, 2022

(54) HYBRID FRAGRANCE ENCAPSULATE FORMULATION AND METHOD FOR USING THE SAME

(71) Applicant: International Flavors & Fragrances Inc., New York, NY (US)

(72) Inventors: Yabin Lei, Holmdel, NJ (US); Michael V. Imperiale, Newark, NJ (US); Lewis M. Popplewell, Morganville, NJ (US); Franklin Pringgosusanto, Laurence Harbor, NJ (US); Ralph Gencarelli, Fairfield, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/057,127

(22) Filed: Oct. 18, 2013

(65) Prior Publication Data

US 2014/0044761 A1 Feb. 13, 2014

Related U.S. Application Data

(63) Continuation-in-part of application No. 13/422,090, filed on Mar. 16, 2012, now Pat. No. 10,099,194, which is a continuation-in-part of application No. 12/793,911, filed on Jun. 4, 2010, now Pat. No. 9,044,732, which is a continuation of application No. 12/328,340, filed on Dec. 4, 2008, now abandoned.

(60) Provisional application No. 61/453,977, filed on Mar. 18, 2011.

(51) Int. Cl.
| | |
|---|---|
| *A61K 9/48* | (2006.01) |
| *A61K 8/11* | (2006.01) |
| *A61Q 15/00* | (2006.01) |
| *C11B 9/00* | (2006.01) |
| *C11D 3/50* | (2006.01) |
| *C11D 17/00* | (2006.01) |
| *A61K 8/73* | (2006.01) |
| *A61Q 13/00* | (2006.01) |
| *A61K 8/25* | (2006.01) |
| *A61Q 5/12* | (2006.01) |
| *A61Q 5/02* | (2006.01) |
| *A61Q 11/00* | (2006.01) |
| *A61Q 19/10* | (2006.01) |
| *B01J 13/20* | (2006.01) |
| *B01J 13/18* | (2006.01) |

(52) U.S. Cl.
CPC .............. *A61K 9/4833* (2013.01); *A61K 8/11* (2013.01); *A61K 8/25* (2013.01); *A61K 8/732* (2013.01); *A61Q 13/00* (2013.01); *A61Q 15/00* (2013.01); *B01J 13/18* (2013.01); *B01J 13/206* (2013.01); *C11B 9/00* (2013.01); *C11D 3/505* (2013.01); *C11D 17/0039* (2013.01); *A61K 2800/412* (2013.01); *A61K 2800/56* (2013.01); *A61Q 5/02* (2013.01); *A61Q 5/12* (2013.01); *A61Q 11/00* (2013.01); *A61Q 19/10* (2013.01)

(58) Field of Classification Search
CPC ................................ C11D 3/505; C11D 3/502
See application file for complete search history.

(56) References Cited

U.S. PATENT DOCUMENTS

| | | | |
|---|---|---|---|
| 2,661,349 A * | 12/1953 | Caldwell ................. | C08B 31/04 536/63 |
| 4,081,384 A | 3/1978 | Pracht ........................... | 510/523 |
| 4,234,627 A | 11/1980 | Schilling ........................... | 8/137 |
| 4,605,554 A | 8/1986 | Prussin et al. | |
| 5,112,688 A | 5/1992 | Michael ...................... | 428/402.2 |
| 5,145,842 A | 9/1992 | Driedger et al. ............. | 514/63 |
| 5,176,903 A | 1/1993 | Goldberg et al. ............. | 424/66 |
| 5,185,155 A * | 2/1993 | Behan ....................... | B01J 13/02 424/451 |
| 5,492,870 A | 2/1996 | Wilcox et al. | |
| 6,194,375 B1 | 2/2001 | Ness et al. ........................ | 512/4 |
| 6,238,650 B1 | 5/2001 | Lapidot et al. ................. | 424/59 |
| 6,248,703 B1 | 6/2001 | Finucane et al. ............. | 510/152 |
| 6,303,149 B1 | 10/2001 | Magdassi et al. ............. | 424/489 |
| 6,329,057 B1 | 12/2001 | Dungworth et al. .......... | 428/403 |
| 6,337,089 B1 | 1/2002 | Yoshioka et al. ............. | 424/451 |
| 6,537,583 B1 | 3/2003 | Dupuis et al. | |
| 6,855,335 B2 | 2/2005 | Seok et al. ..................... | 424/489 |
| 7,112,339 B1 | 9/2006 | Ahola et al. | |

(Continued)

FOREIGN PATENT DOCUMENTS

| | | |
|---|---|---|
| EP | 0478326 A1 | 4/1992 |
| EP | 1627573 A1 | 2/2006 |

(Continued)

OTHER PUBLICATIONS

Gianfrancesco et al., Dairy Sci. Technol., 88: 53-64 (2008).*

(Continued)

*Primary Examiner* — Tigabu Kassa
*Assistant Examiner* — Ivan A Greene
(74) *Attorney, Agent, or Firm* — Licata & Tyrrell P.C.

(57) ABSTRACT

A hybrid encapsulate formulation obtained by mixing a starch/fragrance emulsion with a core-shell capsule suspension is provided as is a method of using the formulation in a personal care product, a beauty care product, a fabric care product, a home care product, a personal hygiene product, an oral care product and a method for releasing an encapsulated fragrance by moisture, shear, or a combination thereof.

18 Claims, 4 Drawing Sheets

(56) References Cited

U.S. PATENT DOCUMENTS

| | | | | |
|---|---|---|---|---|
| 7,147,915 | B2 | 12/2006 | Kawai et al. | 428/402.2 |
| 7,758,888 | B2 | 7/2010 | Lapidot et al. | 424/489 |
| 2002/0064541 | A1* | 5/2002 | Lapidot | A61P 3/02 424/401 |
| 2003/0082276 | A1* | 5/2003 | Subramaniam | A23G 3/346 426/89 |
| 2004/0175404 | A1 | 9/2004 | Shefer et al. | |
| 2005/0153135 | A1 | 7/2005 | Opplewell et al. | |
| 2005/0265938 | A1 | 12/2005 | Cohen et al. | |
| 2006/0256748 | A1 | 11/2006 | Jung et al. | |
| 2007/0026083 | A1* | 2/2007 | Doney | A61K 9/1617 424/490 |
| 2007/0051274 | A1 | 3/2007 | Saito et al. | 106/287.1 |
| 2007/0078071 | A1* | 4/2007 | Lee | A61K 8/11 510/130 |
| 2007/0190325 | A1 | 8/2007 | Berg-Schultz et al. | |
| 2007/0227398 | A1 | 10/2007 | Lee et al. | |
| 2008/0317795 | A1 | 12/2008 | Fraynor et al. | |
| 2009/0004418 | A1 | 1/2009 | Takaki et al. | |
| 2009/0047230 | A1 | 2/2009 | Caballero et al. | |
| 2009/0246279 | A1 | 10/2009 | Kong et al. | 424/486 |
| 2009/0253612 | A1 | 10/2009 | Mushock et al. | 512/4 |
| 2010/0143422 | A1* | 6/2010 | Popplewell | C11D 3/505 424/401 |

FOREIGN PATENT DOCUMENTS

| | | |
|---|---|---|
| EP | 2025364 A2 | 2/2009 |
| EP | 2196257 A2 | 6/2010 |
| EP | 2500087 A2 | 9/2012 |
| FR | 2703927 A1 | 10/1994 |
| FR | 2780901 A1 | 1/2000 |
| GB | 2416524 A | 2/2006 |
| WO | WO94/04260 | 3/1994 |
| WO | WO94/04261 | 3/1994 |
| WO | WO99/03450 | 1/1999 |
| WO | 03/034979 A2 | 5/2003 |
| WO | 03066209 A1 | 8/2003 |
| WO | 2005/009604 A1 | 2/2005 |
| WO | 2008144734 A1 | 11/2008 |
| WO | 2009106318 A2 | 9/2009 |
| WO | 2011003805 A2 | 1/2011 |
| WO | 2011124706 A1 | 10/2011 |
| WO | 2011161265 A2 | 12/2011 |
| WO | 00/09652 A2 | 9/2012 |
| WO | 2013092958 A1 | 6/2013 |

OTHER PUBLICATIONS

Veith, Susanne R. et al.; "Aroma Retention in Sol-Gel-Made Silica Particles," 2004; ACS, Journal of Agricultural and Food Chemistry, vol. 52, No. 19, pp. 5964-5971. (Year: 2004).* van Soest J.J.G. (2007) Encapsulation of Fragrances and Flavours: a Way to Control Odour and Aroma in Consumer Products. In: Berger R.G. (eds) Flavours and Fragrances. Springer, Berlin, Heidelberg, pp. 439-455. (Year: 2007).*

Soottitantawat et al.; "Microencapsulation of l-menthol by spray drying and its release characteristics,"2005, ELSEVIER; Innovative Food Science & Emerging Technologies, vol. 6, pp. 163-170. (Year: 2005).*

Dokic et al.; "Physicochemical characteristics and stability of oil-in-water emulsions stabilized by OSA starch,"2012, ELSEVIER; Food Hydrocolloids, vol. 29, pp. 185-192. (Year: 2012).*

Trubiano; The Role of Specialty Food Starches in Flavor Encapsulation, from Ho et al.; Flavor Technology—ACS Symposium Series, vol. 610, (1997), Chapter 19, pp. 244-253. (Year: 1997).*

Dissertation of Savitha Krishnan—Dec. 2008, The Graduate School of the University of Minnesota, (Copyright 2009, ProQuest LLC, pp. 1-168. (Year: 2008).*

Li, Jason Z.; The Use of Strach-Based Materials for Microencapsulation, from A.G. Gaonkar, N. Vasisht, A.R. Khare, R. Sobel (Eds): Microencapsulation in the Food Industry, Chapter 18, pp. 195-210. (Year: 2014).*

Dickinson, Eric; "Hydrocolloids as emulsifiers and emulsion stabilizers," 2009; ELSEVIER; Food Hydrocolloids, vol. 23, pp. 1473-1482. (Year: 2009).*

Lewis, Richard J.; "Hawley's Condensed Chemical Dictionary, 15th ed.," 2007, entries for "emulsion" and "mixtrue" pp. 499 & 852. (Year: 2007).*

Flick, E.W. "An Industrial Guide" *Cosmetic Additives* Park Ridge, New Jersey: Noyes Publications, 1991 p. 194.

O'Sullivan et al. "Silica-Shell/Oil-Core Microcapsules with Controlled Shell Thickness and Their Breakage Stress" Langmuir 2009 25(14):7962-7966.

Extended European Search Report dated Sep. 25, 2015 from European Patent Office for Application No. 14189395.8, filed Oct. 17, 2014.

BASF publication, title: PVP and More.. Luvitec, Luvicross and Clooacral Val versitle specialty polymers for technical applications, download from http://www.micronal.de/portal/streameron Aug. 6, 2014, published Apr. 2009.

Larsson et al., Annual Transactions of the Nordic Rheology Society, vol. 20 (2012).

Office Communication dated Mar. 15, 2012 from U.S. Appl. No. 12/328,340, filed Dec. 4, 2008.

Office Communication dated Oct. 16, 2012 from U.S. Appl. No. 12/793,911, filed Jun. 4, 2010.

Office Communication dated May 9, 2013 from U.S. Appl. No. 12/793,911, filed Jun. 4, 2010.

Office Communication dated Aug. 22, 2013 from U.S. Appl. No. 13/422,090, filed Mar. 16, 2012.

Mamoru Aizawa Aizawa et al. 2000. Preparation of Spherical Hydrous Silica Oxide Particles under Acidic Condition via Sol-Gel Processing. Journal of Sol-Gel Science and Technology. 19:329-332.

Zuropean Search Report. EP14189284. International Flavors & Fragrances Inc. Feb. 2, 2015.

"Non-Defatting Body Wash", Cosmetic & Toiletry Formulations 2nd Ed. Vol. 2, Flick, Ed. p. 99 (1992).

Hofer et al., Langmuir, 14:4014-4020 (2001).

Zxtended European Search Report dated May 13, 2015 from European Patent Office for Application No. 12159991.4, filed Mar. 16, 2012.

* cited by examiner

HYBRID FRAGRANCE ENCAPSULATE FORMULATION AND METHOD FOR USING THE SAME

INTRODUCTION

This application is a continuation-in-part of U.S. application Ser. No. 13/422,090, filed Mar. 16, 2012, which claims benefit of priority from U.S. Provisional Application Ser. No. 61/453,977, filed Mar. 18, 2011; and is a continuation-in-part of U.S. application Ser. No. 12/793,911, filed Jun. 4, 2010, which is continuation-in-part of U.S. application Ser. No. 12/328,340, now abandoned, filed Dec. 4, 2008, the contents of which are incorporated herein by reference in their entireties.

BACKGROUND

Spray-drying is a well known technique for the encapsulation of flavors and fragrances. Spray-dried products are commonly prepared from an emulsion that is sprayed into a drying chamber. A number of emulsion parameters influence the quality of the spray-dried capsules. For example, to achieve a spray-dried product of relatively small droplet size, the emulsion preferably remains stable during the duration of the spray-drying process, which can vary from a few minutes to several hours. The stability of the droplet size in the emulsion is even more important and difficult to achieve when high amounts of flavors or fragrances are intended to be encapsulated.

In certain instances, biopolymers with surface active properties, such as for example Gum arabic, starches, cellulose, gelatin, alginates or even proteins such as albumin or beta-globulin, are used as emulsifiers. For example, US 2009/0253612 describes a spray-dry encapsulation process for flavor or fragrance comprising drying an aqueous emulsion containing the oil to be encapsulated, modified starch and phosphate salts. Furthermore, an antiperspirant/deodorant containing microcapsules is disclosed in U.S. Pat. No. 5,176,903, where a fragrance oil and ester are encapsulated by a food starch and polysaccharide composition.

SUMMARY OF THE INVENTION

The present invention is a hybrid encapsulate formulation obtained by a method including the steps of preparing an aqueous starch solution; preparing an oil phase containing an active material; emulsifying the oil phase with an aqueous starch solution to obtain an emulsion; mixing the emulsion with a core-shell capsule suspension; and spray drying the mixture to obtain a hybrid encapsulate formulation. In some embodiments, the aqueous starch solution further (optionally) includes maltose, sucrose, maltodextrin, or a combination thereof. In other embodiments, the oil phase optionally includes monoglycerides, lecithin, or a combination thereof. In still further embodiments, the active material is a fragrance oil. In yet other embodiments, the core-shell capsule suspension includes a sol-gel capsule, a hydrogel capsule, a polyurea capsule, an aminoplast capsule, a gelatin capsule, a urea-formaldehyde capsule or a melamine-formaldehyde capsule, which encapsulates an active material, e.g., a fragrance oil. In some embodiments, the core-shell capsule suspension includes a nonionic polymer (e.g., polyvinylpyrrolidone, polyvinyl alcohol, polyethylene glycol, polyethylene oxide, polyethylene oxide-polypropylene oxide, polyethylene oxide-polypropylene oxide-polyethylene oxide, or a combination thereof), cationic polymer (e.g., Polyquaterium-6, Polyquaternium-11, Polyquaternium-47, or a combination thereof), anionic polymer (e.g., a polystyrene sulfonic acid, polyacrylic acid, hyaluronic acid, sodium alginate, sodium carboxymethylcellulose, or a combination thereof), anionic surfactant (e.g., sodium laureth sulfate, complex ester of phosphoric acid and ethoxylated cosmetic grade oleyl alcohol, or a combination thereof), or a combination thereof. In other embodiments the starch/core-shell capsule are at a ratio in the range of 10/90 to 90/10 on a dry weight basis). A personal care product (e.g., an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant, shampoo, hair conditioner, hair rinse, hair refresher, body wash, soap), beauty care product (e.g., fine fragrance or Eau De Toilette), fabric care product (e.g., a rinse conditioner, liquid detergent or powder detergent), home care product (e.g., an all-purpose cleaner or fabric refresher), personal hygiene product (e.g., hand sanitizer) or oral care product (e.g., tooth powder) containing the hybrid encapsulate formulation is also provided, as is a method for releasing an encapsulated fragrance by moisture, shear, or a combination thereof.

DETAILED DESCRIPTION OF THE INVENTION

Figure 1:
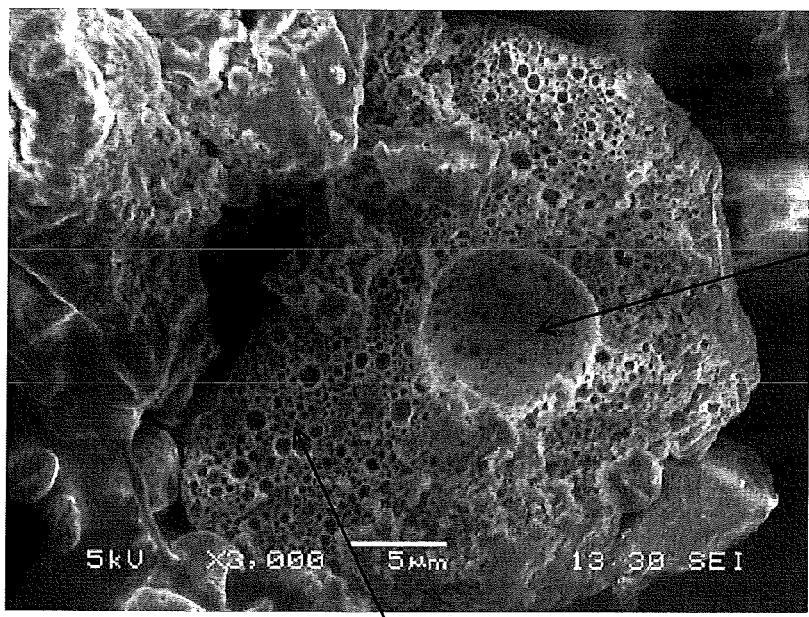
FIG. 1 shows a SEM micrograph of a fragrance encapsulate prepared with starch. 1, characteristic air pocket in center; 2, small pores (holes) left in oil droplets.

It is often desired to control the release of a perfume or flavor out of a consumer product, in particular when the perfumed or flavored consumer product is intended to produce consumer conceivable benefits at a certain "magic moment" under a wide variety of user environments. This invention concerns hybrid encapsulate formulations that can provide variable and multistage release of encapsulated materials. The release of encapsulated active materials, such as fragrances, can be triggered either by moisture or shear to provide multi-stage release profiles. The hybrid formulations are suitable for a wide range of personal applications including, but not limited to, antiperspirant and deodorant products.

Accordingly, this invention is a hybrid encapsulate formulation obtained by preparing an aqueous starch solution; preparing an oil phase containing an active material; emulsifying the oil phase with the aqueous starch solution to obtain a fragrance emulsion; mixing the fragrance emulsion with a core-shell capsule suspension; and spray drying the mixture. In accordance with the present invention, an aqueous solution is intended to mean a solution in which the solvent is water. As is known in the art, starch is a carbohydrate composed of a large number of glucose units joined by glycosidic bonds. The starch of this invention can be obtained from seeds, roots or tubers, by wet grinding, washing, sieving and drying. Starches are predominantly obtained from corn, wheat and potato, and to a lesser extent, sources such as rice, sweet potato, sago and mung bean. The starch can be unmodified or chemically modified to allow the starch to function under conditions frequently encountered during processing or storage, such as high heat, high shear, low pH, oxidation, freeze/thaw and cooling. Such modifications include, but are not limited to acid treatment, alkaline treatment, bleaching, oxidation, enzyme treatment, acetylation, phosphorylation, or a combination thereof. Typical modified starches include cationic starches, hydroxyethyl starch and carboxymethylated starches. In particular embodiments, the starch is a modified starch. Exemplary modified starches include, but are not limited to, CAPSUL, CAPSUL FP, HI-CAP IMF, HI-CAP 100 and the like. In one embodiment, the aqueous starch solution optionally includes maltose, sucrose, maltodextrin, or a combination thereof. In another embodiment, the aqueous starch solution also optionally includes a cellulose ether, e.g., METHOCEL.

The oil phase of the invention is intended to include oil soluble ingredients. The oil phase can be composed of the active material alone (e.g., a fragrance oil) or include other components such as surfactants or emulsifiers. In one embodiment, the oil phase includes the active material in combination with a monoglyceride, lecithin, or a combination thereof. In certain embodiments, the active material is a fragrance oil, essential oil, plant extract or mixture thereof, as described herein.

In some embodiments, an active material is also encapsulated within the core-shell capsule. In certain embodiments, the active material is a fragrance oil, essential oil, plant extract or mixture thereof, as described herein. In this respect, the hybrid encapsulate formulation can include a first fragrance (encapsulated in a core-shell capsule) and a second fragrance (present in the oil phase). In some embodiments, the first and second fragrances are the same. In other embodiments, the first and second fragrances are different.

In accordance with the present invention, the ratio of starch/core-shell capsule used in the formulation of this invention is in the range of 10/90 to 90/10 (on a dry weight basis, as provided in the examples). In certain embodiments, the ratio of starch/core-shell capsule is 10/90, 20/80, 30/70, 40/60, 50/50, 60/40, 70/30, 80/20 or 90/10.

Given the variable and multistage release of encapsulated active materials by moisture or shear triggers, this invention also provides a method for releasing an encapsulated fragrance by moisture, shear, or a combination thereof by encapsulating a first fragrance in a core-shell capsule, mixing the core-shell encapsulated fragrance with a fragrance emulsion containing a second fragrance and starch to obtain a hybrid fragrance encapsulate formulation, spray drying the hybrid fragrance encapsulate formulation, incorporating the hybrid fragrance encapsulate formulation into a consumer product base to obtain a consumer product, applying the consumer product containing the hybrid fragrance encapsulate to a surface, and exposing the surface to moisture, shear, or a combination thereof so that the encapsulated fragrance is released. In some embodiments, the encapsulated materials are released in two stages. In one embodiment, the encapsulated material is first released by moisture and then by shear. In a second embodiment, the encapsulated ingredient is first released by shear and then by moisture. The fragrance encapsulate can provide instant release of fragrance by either moisture activation or shear force depending on the environments and application needs. It will also enable the release of encapsulated fragrance ingredients at different time points by shear. Therefore, the invention provide a system that can provide perfumery benefits at different consumer needed "magic moments" by varying release mechanism and release at different application points under a range of application environments.

Core-Shell Encapsulation Systems.

Encapsulation of active material such as fragrances is known in the art, see for example U.S. Pat. Nos. 2,800,457, 3,870,542, 3,516,941, 3,415,758, 3,041,288, 5,112,688, 6,329,057, and 6,261,483. Wall forming materials include polyurethane, polysiloxanes, polyurea, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, microcapsules can be made via the simple or complex coacervation of gelatin. Preferred encapsulating polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts.

Aminoplasts.

A representative process used for aminoplast encapsulation is disclosed in U.S. Pat. No. 3,516,941, though it is recognized that many variations with regard to material and process steps are possible. A representative process used for gelatin encapsulation is disclosed in U.S. Pat. No. 2,800,457, though it is recognized that many variations with regard to material and process steps are possible. Both of these processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB GB2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-Formaldehyde and Melamine-Formaldehyde Capsules.

Urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or copolymers. Methods for formation of such melamine-formaldehyde and urea-formaldehyde pre-condensates are set forth in U.S. Pat. Nos. 3,516,846, 6,261,483, and Lee et al. (2002) *J. Microencapsulation* 19:559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

Polyurea Capsules.

Polyurea capsules are also well-known in the art. For example, isocyanate-based capsule wall technologies are disclosed in WO 2004/054362; EP 0 148149; EP 0 017 409 B1; U.S. Pat. Nos. 4,417,916, 4,124,526, 5,583,090, 6,566,306, 6,730,635, WO 90/08468, WO 92/13450, U.S. Pat. Nos. 4,681,806, 4,285,720 and 6,340,653.

Suitable isocyanates of use in this invention include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

To facilitate wall formation, polyurea capsules can also include cross-linking agents, such as amines or alcohols. Examples of amines of particular use include guanidine amines/salts, amphoteric amines, diamines or a combination thereof.

Water soluble diamines are one class of amines of use in this invention as the amine is usually present in the aqueous phase. One class of such amine is of the type:

where n is ≥1. When n is 1, the amine is a diamine, ethylene diamine. When n is 2, the amine is diamine propane and so on. Exemplary amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are the polyalykylene polyamines of the type:

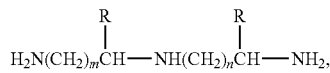

where R equals hydrogen or —$CH_3$, m is 1-5 and n is 1-5, e.g., diethylene triamine, triethylene tetraamine and the like. Exemplary amines of this type include, but are not limited to diethylenetriamine, bis(3-aminopropyl)amine, bis(hexamethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

Exemplary polyetheramines include 2,2'-ethylenedioxy)bis(ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, L-arginine, L-lysine monohydrochloride, arginine monohydrochloride and ornithine monohydrochloride.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176 (where x=3) (from Huntsman). Other polyether amines include the JEFFAMINE ED Series, and JEFFAMINE TRIAMINES.

Alcohols of use as cross-linking agents typically have at least two nucleophilic centers. Exemplary alcohols include, but are not limited to, ethylene glycol, hexylene glycol, pentaerythritol, glucose, sorbitol, and 2-aminoethanol.

Hydrogel Capsules.

Hydrogel capsules can be prepared with bi- or polyfunctional vinyl monomers including, but not limited to, allyl methacrylate, triethylene glycol dimethacrylate, ethylene glycol dimethacrylate, diethylene glycol dimethacrylate, aliphatic or aromatic urethane diacrylate, difunctional urethane acrylate, ethoxylated aliphatic difunctional urethane methacrylate, aliphatic or aromatic urethane dimethacrylate, epoxy acrylate, epoxymethacrylate, tetraethylene glycol dimethacrylate, polyethylene glycol dimethacrylate, 1,3 butylene glycol diacrylate, 1,4-butanediol dimethacrylate, 1,4-butaneidiol diacrylate, diethylene glycol diacrylate, 1,6 hexanediol diacrylate, 1,6 hexanediol dimethacrylate, neopentyl glycol diacrylate, polyethylene glycol diacrylate, tetraethylene glycol diacrylate, triethylene glycol diacrylate, 1,3 butylene glycol dimethacrylate, tripropylene glycol diacrylate, ethoxylated bisphenol diacrylate, ethoxylated bisphenol dimethylacrylate, dipropylene glycol diacrylate; alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, ethoxylated trimethylolpropane triacrylate, propoxylated trimethylolpropane triacrylate, propoxylated glyceryl triacrylate, ditrimethyloipropane tetraacrylate, dipentaerythritol pentaacrylate, ethoxylated pentaerythritol tetraacrylate, or a combination thereof.

Hydrogel capsules can be prepared by conventional methods using initiators such as azobisisobutyronitrile (AIBN), sodium persulfate, and benzoyl peroxide. Moreover, emulsifiers may be included during the preparation of hydrogel capsules. By way of illustration, exemplary emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from about 0.1 to about 40 percent by weight of all constituents, more preferably from 0.5 to about 10 percent, more preferably 0.5 to 5 percent by weight.

Sol-Gel Capsules.

Sol-gel precursors, i.e., starting compounds capable of forming gels, suitable for the purposes of the invention are known in the art. Sol-gel precursors usable in accordance with the invention are, for example, compounds that are capable of forming gels including, e.g., silicon, boron, aluminum, titanium, zinc, zirconium and vanadium. The precursors can also include metal alkoxides and diketonates. Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof. One example of sol-gel precursors suitable for the purposes of the invention are alkoxysilanes corresponding to the following general formula: $(R_1O)(R_2O)M(X)(X')$, wherein M is Si, Ti, or Zr; X is equal to hydrogen, or —$OR_3$; X' is equal to hydrogen, or —$OR_4$; and $R_1$, $R_2$, $R_3$ and $R_4$ independently represent an organic group, more particularly a linear or branched alkyl group, preferably a $C_{1-12}$ alkyl.

As indicated, the microcapsules of this invention can be prepared by conventional methods to encapsulate one or more active materials. In some embodiments, the active material is encapsulated by a polymer in the presence of a capsule formation aid, e.g., a surfactant or dispersant. Classes of protective colloid or emulsifier of use as surfactants or dispersants include maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, carboxymethyl cellulose, fatty acid esters of polyoxyethylenated sorbitol and sodium dodecylsulfate.

Commercially available surfactants include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Typically, hydrocolloids or adjuvants are used to improve the colloidal stability of the capsule suspension or slurry against coagulation, sedimentation and creaming. As such, such processing aids can also be used in conjunction with the microcapsules of this invention. As used herein, the term "hydrocolloid" refers to a broad class of water-soluble or water-dispersible polymers having anionic, cationic, zwitterionic or nonionic character. In particular embodiments, the capsule suspension includes a nonionic polymer, cationic polymer, anionic polymer, anionic surfactant, or a combination thereof. In certain embodiments, the nonionic polymer is a polyvinylpyrrolidone (PVP), polyvinyl alcohol (PVA) polyethylene glycol (PEG), Polyethylene oxide (PEO), or polyethylene oxide-polypropylene oxide (PEO-PPO), polyethylene oxide-polypropylene oxide-polyethylene oxide (PEO-PPO-PEO). In other embodiments, the cationic polymer is Polyquaterium-6 (polydiallyldimethylammonium chloride), Polyquaternium-11 (vinyl pyrrolidone/dimethylaminoethyl methacrylate copolymer) or Polyquaternium-47 (acrylic acid/methacrylamidopropyl trimethyl ammonium chloride/methyl acrylate terpolymer). In yet other embodiments, the anionic polymer is a polystyrene sulfonic acid, polyacrylic acid, hyaluronic acid, sodium alginate, or sodium carboxymethylcellulose (CMC). In still other embodiments, the anionic surfactant is sodium laureth sulfate (SLS) or a complex ester of phosphoric acid and ethoxylated cosmetic grade oleyl alcohol (e.g., CRODAFOS 010A-SS-(RB)).

Other hydrocolloids useful in the present invention include polycarbohydrates, such as starch, modified starch, dextrin, maltodextrin, and cellulose derivatives, and their quaternized forms; natural gums such as alginate esters, carrageenan, xanthanes, agar-agar, pectins, pectic acid, and natural gums such as gum arabic, gum tragacanth and gum karaya, guar gums and quaternized guar gums; gelatin, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth) acrylate-co-(meth)acrylic acid), poly(acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and their quartenized forms.

The diameter of the capsules produced in accordance with this invention can vary from about 10 nanometers to about 1000 microns, preferably from about 50 nanometers to about 100 microns and is most preferably from about 2 to about 15 microns. The capsule distribution can be narrow, broad, or multi-modal. Multi-modal distributions may be composed of different types of capsule chemistries.

Active Material.

Active materials suitable for use in this invention include without limitation, any combination of fragrance oil, essential oil, plant extract or mixture thereof that is compatible with, and capable of being encapsulated by, a polymer. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile); iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H—)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert-butyl-(2,4-dimethyl-3-cyclohexen-1-yl) ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and aralipathic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methyl-N-methylanthranilate, Schiff's bases of methyl anthranilate with 7-hydroxy-3,7-dimethyloctanal, 2-methyl-3-(4-tert-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemongrass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total core-shell capsule suspension or capsule slurry, preferably from about 60% to about 10% of the total capsule suspension or capsule slurry, and most preferably from about 50% to about 20% of the total capsule suspension or capsule slurry.

In some embodiments, the amount of encapsulated fragrance oil is from about 5% to about 60% of the total weight of the hybrid encapsulate formulation, preferably from about 10% to about 50% of the total weight of the hybrid encapsulate formulation.

In addition to the fragrance materials, the present invention also contemplates the incorporation of other core additives including solvent, emollients, particles, polymeric core modifiers and/or core modifier materials encapsulated by the encapsulating polymer.

Solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater than 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should denoted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerin. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO$—[$OCH_2$—$CH(OCOR_1)$—$CH2O$—]$_n$, where $R_1$ and $R_2$ can be H or C4-26 aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIO-SOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isononanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DEMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

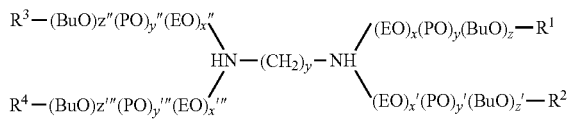

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Other active materials that can be included the in capsules of this invention include antimicrobial agents such as thymol, 2-hydroxy-4,2,4-trichlorodiphenylether, triclocarban; organic sunscreen actives such as oxybenzone, octylmethoxy cinnamate, butylmethoxy dibenzoyln ethane, p-aminobenzoic acid and octyl dimethyl-p-aminobenzoic acid; vitamins such as Vitamin A, Vitamin C and Vitamin E or esters thereof; and malodor counteracting ingredients including, but not limited to, an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, and zinc undecenylate.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus, the fragrances of the invention can be used to alter the aroma characteristics of the perfume composition by modifying the olfactory reaction contributed by another ingredient in the composition. The amount will vary depending on many factors including other ingredients, their relative amounts and the effect that is desired.

Spray-drying typically includes breaking up an emulsion into droplets of desired size, e.g., in a spray nozzle, from a spinning disc, or apertured centrifugal atomizer, and removing moisture in a drying environment to solidify the coating material in the droplets to form solid particles. The drying environment preferably is hot drying air, e.g., in a spray-drying tower. The particles produced by this process, are characterized by a cellular structure composed of many dispersed globules of the core material in a matrix of the coating material. Any suitable method of spray-drying can be used in conjunction with this invention including, but is not limited to, spray-drying tower or continuous fluidized bed spray granulation (see, for example, WO 00/36931). Useful spray towers include dryers from Anhydro, Niro or Nubilosa.

Applications.

The present invention is well-suited for use in personal care products including, without limitation, deodorants and antiperspirants, shampoos, hair conditioners, hair rinses, hair refreshers, body washes, soaps products and the like. In particular embodiments, the formulation of the invention is of use in an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant. Exemplary personal care product formulations are provided in Examples 8-14.

The present invention is also well-suited for use in fabric care products such as rinse conditioners and liquid and powder detergents; home care products such as all-purpose cleaners and fabric refreshers; personal hygiene products such as hand sanitizers; and oral care products such as tooth powder, all of which are known in the art. For example, liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065.

The invention is described in greater detail by the following non-limiting examples.

Example 1

Preparation of Core-Shell Silica Capsules with a Sol-Gel Precursor

This example illustrates the preparation of silica capsules using a precursor where the central silicon atom is coordinated to four alkoxy groups. The empirical formula is $Si(OR)_4$, where —OR is an alkoxy group and is hydrolyzable upon dispersion in water. In general, the method involves preparing a concentrated fragrance emulsification, diluting the fragrance emulsion to the desired concentration, and adding tetraethyl orthosilicate (TEOS).

Preparation of Concentrated Fragrance Emulsion.

Two hundred and six grams fragrance oil was weighed out and placed in a round bottom vessel. In a separate vessel, a 1.0% aqueous surfactant solution (120 g) was prepared by dissolving the needed amount of 30% cetyltrimethylammonium chloride (CTAC) surfactant solution in distilled water. The oil phase was then poured into the aqueous phase and the mixture was homogenized with a high shear mixer (Ultra Turrax T 25 Basic, IKA, Werke). Four drops of defoamer was added to suppress the foaming generated.

Preparation of Diluted Fragrance Emulsion.

Diluted fragrance emulsion was prepared by blending the concentrated fragrance emulsion with the desired amount of water to generate the desired concentration.

Preparation of Silica Capsules.

The formation of silica capsules was achieved by adding a single precursor to the diluted fragrance emulsion. The amount of precursor added was routinely determined by the wall polymer level needed and was generally 1% to 30% of the final formulation. Typically, the desired amount of precursor, TEOS was weighted out (35.91 g in this example) and placed in a clean and dry dropping funnel. The TEOS was then added dropwise into the diluted fragrance emulsion under constant mixing. The mixing speed was reduced once the addition of TEOS was complete. The system was the left at room temperature and cured for an extended period of time. The pH of the system was maintained at approximately 3 to 4. The capsule formed was well dispersed and generally had a particle size ranging from submicron to one hundred micron depending on the emulsifier and shear rates used.

Example 2

Hybrid Spray Fragrance Encapsulation Formulations

Hybrid silica gel capsule/starch formulations composed of three parts were prepared as follows.

Preparation of Part A.

Part A was prepared by weighing out the desired amount of tap water and CAPSUL Starch (National Starch, Bridgewater, NJ) into a suitable container. The mixture was then heated to 50 to 55° C. and Maltose (Mitsubishi, Japan) and METHOCEL cellulose ethers (Dow Chemical, Middle Land, Mich.) were added. The mixture was kept at 55° C. and stirred with an overhead mixer until a homogeneous solution was obtained. Part A was cooled to 19° C. by submersion in an ice bath to prevent pre-mature volatilization of fragrance ingredients.

Preparation of Part B.

Part B was prepared by weighing out the desired amount of DIMODAN PH320 (distilled monoglyceride; Dow Chemical, Middle Land, Mich.) and heating it until the material was liquefied. The desired amount of fragrance was then added with constant mixing until a homogenous phase was obtained.

Preparation of Part C.

Part C was prepared by preparing a 30% LUVISKOL K-30 (Polyvinylpyrrolidone; BASF) by dissolving solid LUVISKOL K30 into deionized water. The solution was then mixed into silica capsule slurry under constant stirring. The mixing continued for an additional 30 minutes to ensure a homogenous mixture was obtained.

Preparation of Fragrance Emulsion.

A fragrance emulsion was prepared by adding Part B into Part A. The mixture was subject to mixing with a high shear homogenizer (Greerco, Model 11, 2001 with Baldor Industrial Motor), while still submerged in an ice-bath. The prepared emulsion had a particle size of 3 microns.

Preparation of Solution for Spray Dry.

The mixture of Part C was combined with the fragrance emulsion under consistent stirring with an overhead mixer. This mixture was then fed into a Niro Spray Drier. The inlet temperature was maintained at 190° C. and the emulsion was fed at a rate sufficient to maintain exit air temp at 90° C.

Formulations containing different ratios of fragrance emulsion to capsule slurry were prepared, each containing a 45.1% fragrance load. Formula 1 (Table 1; 90/10 ratio) and Formula 2 (Table 2; 70/30 ratio) were prepared as above. Formula 3 (Table 3; 90/10 ratio) and Formula 4 (Table 4; 70/30 ratio) were prepared as above, however, the fragrance was added directly to the starch solution. Formula 5 (Table 5; 90/10 ratio) and Formula 6 (Table 6; 70/30 ratio) were prepared as above, however, the fragrance was added directly to the starch solution, which was composed of HI-CAP 100 (modified food starch derived from waxy maize).

In the context of this invention, the ratio of starch/core-shell capsule is defined as the dry weight of starch to that of the core-shell capsule suspension minus the amount of water in the suspension. Thus, the dry weight of the core-shell capsule is the cumulative weight of the capsule wall polymer, the oil/fragrance core, and the capsule formation aid used in preparing the core-shell capsule.

TABLE 1

| Part | Ingredient | Parts* | Dry Weight (%) |
|---|---|---|---|
| A | City Water | 880.000 | |
| | CAPSUL Starch | 416.000 | 41.600 |
| | Maltose | 41.200 | 4.120 |
| | METHOCEL A4M | 23.000 | 2.300 |
| B | DIMODAN PH 320 | 17.000 | 1.700 |
| | Fragrance | 382.800 | 38.280 |
| C | LUVISKOL K-30 30% soln | 20.000 | 2.000 |
| | Silica capsule slurry | 100.000 | 10.000 |
| | Total Solid Input: | 1000.000 | 100.000 |

*Units, grams

TABLE 2

| Part | Ingredient | Parts* | Dry Weight (%) |
|---|---|---|---|
| A | City Water | 665.0 | |
|   | CAPSUL Starch | 383.5 | 38.35 |
|   | Maltose | 46.0 | 4.6 |
|   | METHOCEL A4M | 23.000 | 2.300 |
| B | DIMODAN PH 320 | 13.0 | 1.300 |
|   | Fragrance | 199.5 | 19.95 |
| C | LUVISKOL K-30 30% soln | 35.000 | 3.5 |
|   | Silica capsule slurry | 300.000 | 230.0 |
|   | Total Solid Inputs: | 1000.000 | 100.00 |

*Units, grams

TABLE 3

| Part | Ingredient | Parts* | Dry Weight (%) |
|---|---|---|---|
| A | City Water | 834.0 | |
|   | Capsule Starch | 452.0 | 45.2 |
|   | Maltose | 46.0 | 4.6 |
|   | Fragrance | 382.0 | 38.2 |
| B | LUVISKOL K-30 30% soln | 20.0 | 2.0 |
|   | Silica capsule slurry | 100 | 10 |
|   | Total Solid Inputs: | 1000.000 | 100.00 |

*Units, grams

TABLE 4

| Part | Ingredient | Parts* | Dry Weight (%) |
|---|---|---|---|
| A | City Water | 665.0 | |
|   | Capsule Starch | 411.5 | 41.15 |
|   | Maltose | 54.0 | 5.4 |
|   | Fragrance | 199.5 | 19.95 |
| B | LUVISKOL K-30 30% soln | 35 | 3.5 |
|   | Silica capsule slurry | 300 | 30 |
|   | Total Solid Inputs: | 1000.000 | 100.00 |

*Units, grams

TABLE 5

| Part | Ingredient | Parts* | Dry Weight (%) |
|---|---|---|---|
| A | City Water | 880.0 | |
|   | HI-CAP 100 | 498.0 | 49.8 |
|   | Fragrance | 382.0 | 38.2 |
| B | LUVISKOL K-30 30% soln | 20.0 | 2.0 |
|   | Silica capsule slurry | 100.0 | 10 |
|   | Total Solid Inputs: | 1000.000 | 100.00 |

*Units, grams

TABLE 6

| Part | Ingredient | Parts* | Dry Weight (%) |
|---|---|---|---|
| A | City Water | 665.0 | |
|   | HI-CAP 100 | 415.0 | 41.5 |
|   | Fragrance | 250.0 | 25.0 |
| B | LUVISKOL K-30 30% soln | 35.0 | 3.5 |
|   | Silica capsule slurry | 300.0 | 30.0 |
|   | Total Solid Inputs: | 1000.000 | 100.00 |

*Units, grams

Example 3

Physical Characterization of Hybrid Fragrance Encapsulate

Figure 2:
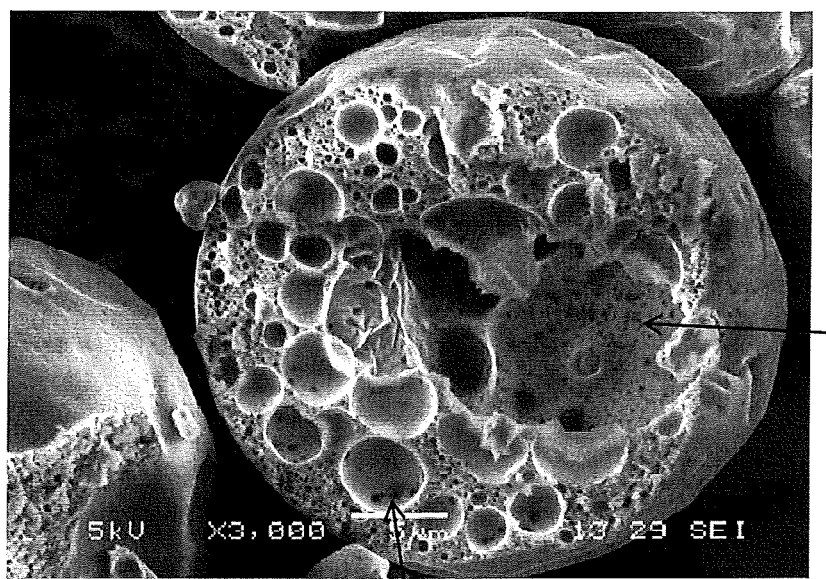
FIG. 2 shows a SEM micrograph of a fragrance encapsulate prepared in accordance with the present invention. 1, characteristic air pocket in center; 3, larger holes (1-5 µm) left by capsules that were imbedded into the SD.

Scanning Electron Microscopy (SEM) was used to characterize the formulation of the present invention. The samples were cut with a doctor blade. A fragrance encapsulate prepared with starch only (FIG. 1) was compared to a fragrance encapsulate prepared according the present invention (FIG. 2). The SEM results clearly show that the fragrance encapsulate of the present invention has large (1-5 µm) holes left by capsules that were embedded into the SD.

Example 4

Fragrance Release Profile of Hybrid Fragrance Encapsulate in Antiperspirant/Stick Triggered by Moisture and Shear To evaluate the performance of the hybrid fragrance encapsulate, a sample prepared according to Formula 6 was formulated into an antiperspirant (AP) stick base (Table 7)

TABLE 7

| Ingredient | Weight (%) |
|---|---|
| Cyclopentasiloxane | to 100% |
| Aluminum Zirconium Tetrachlorohydrex Gly | 22-26% |
| Stearyl Alcohol | 12-15% |
| Hydrogenated Castor Oil (MP80) | 2.5-5.0% |
| Steareth 100 | 0.2-1.0% |
| Mineral Oil | 8-12% |
| Isopropyl Palmitate | 16-20% |
| PPG-14 Butyl Ether | 8-10% |
| C12-C15 Alkyl Benzoate | 14-18% |
| Waxes | 12% |
| polyethylene | 0.5-2% |

Figure 3:
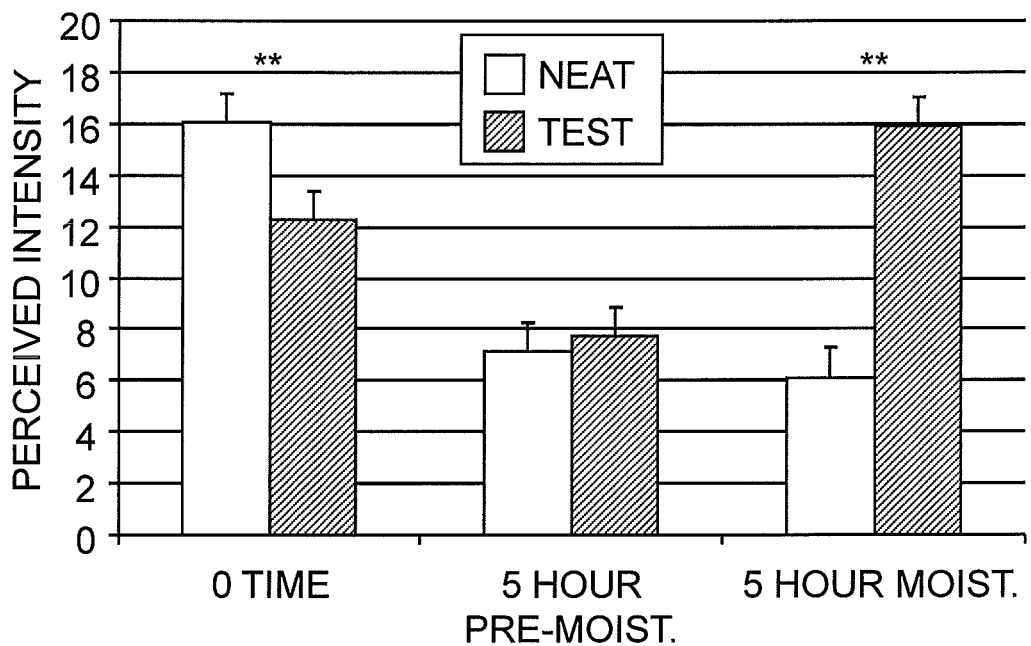
FIG. 3 shows the sensory performance of the fragrance encapsulate prepared in accordance with the present invention (test: encapsulated oil at 0.75% NOE) as compared to neat fragrance (0.75% fragrance) in an antiperspirant stick base, wherein release was triggered by moisture (Moist.).
Figure 4:
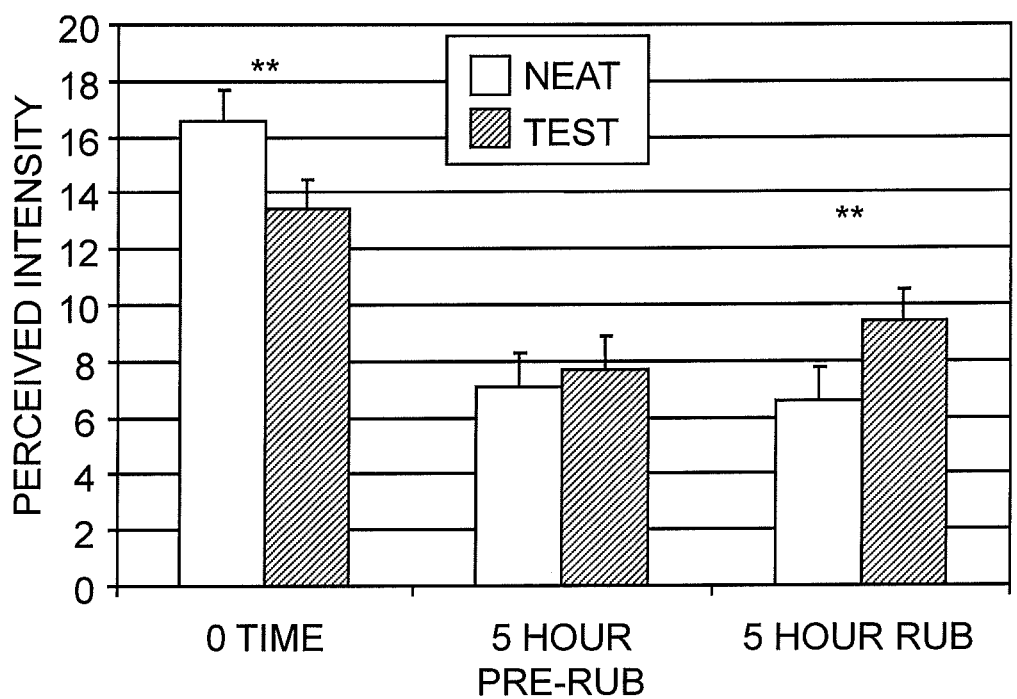
FIG. 4 shows the sensory performance of the fragrance encapsulate prepared in accordance with the present invention (test: encapsulated oil at 0.75% NOE) as compared to neat fragrance (0.75% fragrance) in an antiperspirant stick base, wherein release was triggered by shear (rub).

Performance was evaluated by an internal sensory protocol as follows. Panelists (30-35, with a mix of male and female) were instructed to shower with an unfragranced soap on the day of evaluation. For the comparative analysis, one underarm was applied with the test sample, the other with a control sample. The samples were composed of 0.35 g of AP stick base, weighed and wrapped in wax paper for easy application onto skin. Application of the samples was counterbalanced across underarms. Fragrance intensity was evaluated at 0, 8, 12 and 24 hours after application on a 0-10 intensity scale. Intensity ratings were entered by panelists into an automated data entry system, (COMPUSENSE at-hand) at the designated times. Intensity scores were averaged across panelists for each sample and analyzed by Two-Way ANOVA ($p<0.1/90\%$ CI). The results of this analysis are presented in FIGS. 3 and 4.

Example 5

Sustained and Triggered Release of Capsules in Hybrid Fragrance Encapsulate

Figure 5:
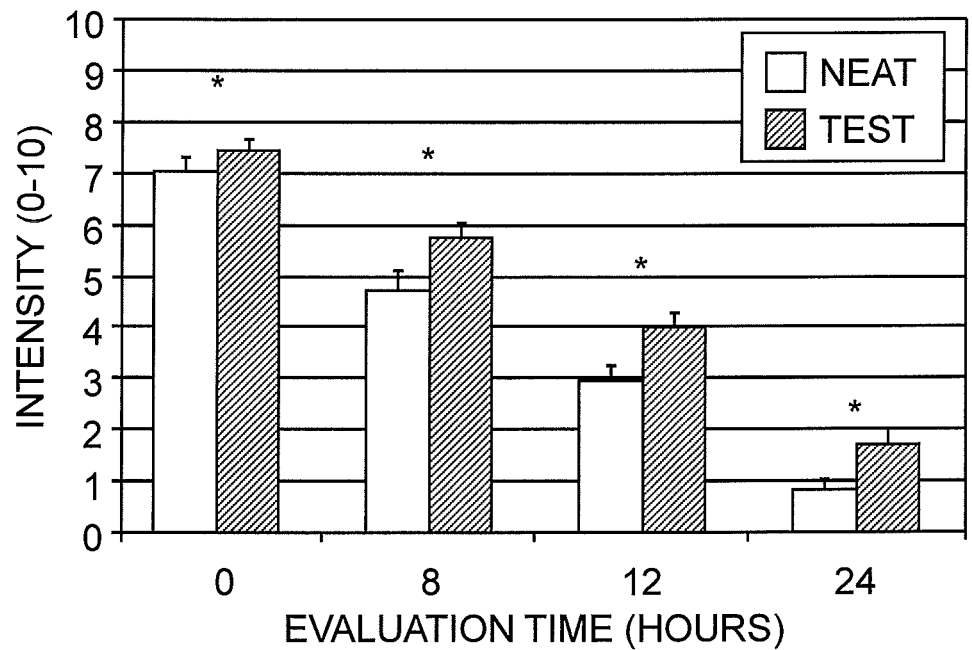
FIG. 5 shows sustained and triggered release performance of the fragrance encapsulate of the invention (test: neat fragrance at 1.75%+encapsulated oil at 0.75% NOE) as compared to neat fragrance (1.75% fragrance) in an antiperspirant stick base. *Confidence level of 90% CI or greater. N=31.

Samples were formulated as described in Example 4 and the performance of the encapsulate was evaluated after 8, 12 and 24 hours. The results of this analysis are presented in FIG. 5. This analysis clearly showed that the formulation containing the encapsulated fragrance prepared according the present invention produced significantly greater intensity at 8, 12 and 24 hours compared to the formulation that only contained neat fragrance.

Example 6

Sensory Evaluation of the Hybrid Fragrance Encapsulate in a AP/Aerosol Base

The performance of the hybrid fragrance encapsulate was also evaluated in an AP/aerosol base formulation (Table 8) using a procedure similar to that described in Example 4, with the exception that application included two sprays of the sample at a distance of 15 cm from the underarm.

TABLE 8

| Ingredient | Weight (%) |
| --- | --- |
| Cyclomethicone | to 100% |
| Aluminum Chlorohydrate | 5-6% |
| Disteardimonium Hectorite | 0.5-1.0% |
| Butane, Isobutane, Propane, 152A | 85-89% |
| Propylene Carbonate | ~0.1% |
| PPG14-Butylene | ~4.0% |
| Isopropyl Palmitate | 0-5.0% |
| Dimethiconol | 0-4.0% |

Figure 6:
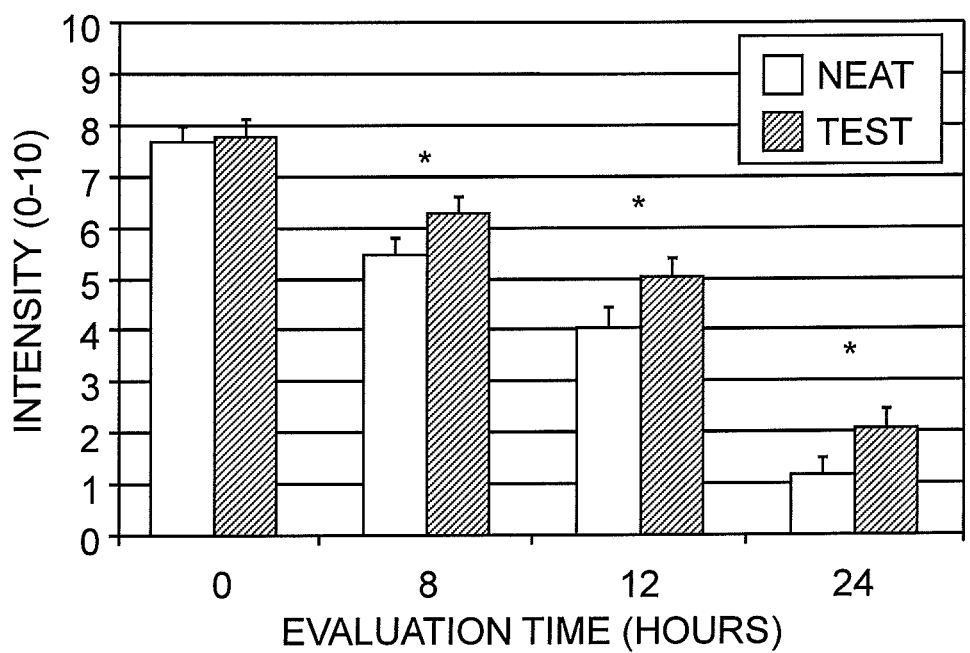
FIG. 6 shows sustained and triggered release performance of the fragrance encapsulate of the invention (test: neat fragrance at 1.0%+encapsulated oil at 0.3% NOE) as compared to neat fragrance (1.0% fragrance) in an antiperspirant aerosol base. *Confidence level of 90% CI or greater.

The results are presented in FIG. 6. This analysis indicates that the formulation containing the encapsulated fragrance of this invention produced significantly greater intensity at 8, 12, and 24 hours compared the formulation that only contained neat fragrance.

Example 7

Stability of Hybrid Fragrance Encapsulate

Figure 7:
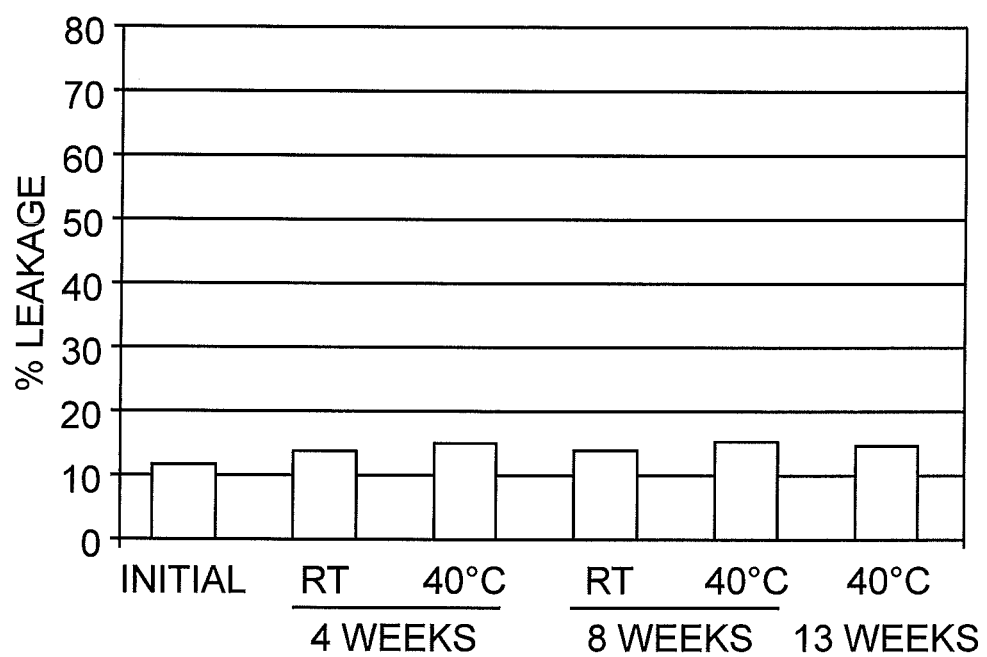
FIG. 7 shows the stability of hybrid fragrance encapsulate samples (encapsulated oil at 0.75% NOE) stored at room temperature (RT) and 40° C. for 4, 8 or 13 weeks.

Samples were prepared by dosing the encapsulated fragrance into an AP/Stick base at 0.75% NOE. Samples were stored at room temperature and 40° C. and the amount of fragrance that leached out of the capsules was measured at different time intervals. As shown in FIG. 7, leakage was less than 20% for all samples even after 13 weeks, demonstrating the robust stability of the formulation of the invention.

Example 8

Clear Deodorant Stick Formulation

An exemplary clear deodorant stick formulation is provided in Table 9.

TABLE 9

| Ingredient | Percentage |
| --- | --- |
| Water | 20 |
| Phosphatidylglycerol/Diphosphatidylglycerol | 55 |
| Sodium Stearate | 6 |
| PEG-4 | 15 |
| Antibacterial Agent | 0.1 |

Example 9

Antiperspirant Emulsion Spray Formulation

An exemplary antiperspirant emulsion spray formulation is provided in Table 10.

TABLE 10

| Ingredient | Percentage |
| --- | --- |
| Water | to 100 |
| Dimethicone | 6 |
| Aluminum Chlorohydrate | 5-6 |
| EDTA | 0.15 |
| Lauryl PEG-9 Polydimethylsiloxyethyl | 0.3 |
| Dimethicone | |
| Phenoxyethanol | 0.3 |
| Isobutane | 70 |

Example 10

Antiperspirant Emulsion Roll-On Formulation

An exemplary antiperspirant emulsion roll-on formulation is provided in Table 11.

TABLE 11

| Ingredient | Percentage |
| --- | --- |
| Water | to 100 |
| Aluminum Chlorohydrate or Aluminum Zirconium Tetrachlorohydrex Gly | 32-36 |
| Steareth-2, Steareth-20 | 0.5-4 |
| Silica | 1-5 |
| Glycerin | 3-5 |
| Dimethicone | 0.5 |

Example 11

Antiperspirant Clear Emulsion Stick Formulation

An exemplary antiperspirant clear emulsion stick formulation is provided in Table 12.

TABLE 12

| Ingredient | Percentage |
| --- | --- |
| Water | 40 |
| Aluminum Zirconium Tetrachlorohydrex Gly | 20 |
| Stearyl Alcohol | 30 |
| C12-C15 Alkyl Benzoate | 25 |
| Glycine | 7 |
| Dimethicone | 0.07 |

Example 12

Antiperspirant Opaque Emulsion Stick Formulation

An exemplary antiperspirant opaque emulsion stick formulation is provided in Table 13.

TABLE 13

| Ingredient | Percentage |
| --- | --- |
| Water | to 100 |
| Aluminum Chlorohydrate | 40 |
| Isopropyl Palmitate | 9 |
| Dimethicone | 5.8 |
| Synthetic Wax | 9 |
| Beheneth-10 | 2 |
| Polyglyceryl-3 Diisosterate | 0.3 |
| Acrylates Copolymer | 0.3 |
| PEG/PPG-18/18 Dimethicone | 2 |
| Phenoxyethanol | 0.5 |
| Pentylene Glycol | 0.5 |
| Cetyl PEG/PPG-10/1 Dimethicone | 2 |

Example 13

Deodorant Spray Formulation

An exemplary deodorant spray formulation is provided in Table 14.

TABLE 14

| Ingredient | Percentage |
| --- | --- |
| Denatured Alcohol | 45 |
| Polyaminopropyl biguanide stearate | 0.2-0.5 |
| Butane, Isobutane, Propane, 152A | 55 |

Example 14

Antiperspirant Clear Gel Formulation

An exemplary antiperspirant clear gel formulation is provided in Table 15.

TABLE 15

| Ingredient | Percentage |
| --- | --- |
| Water | 20 |
| Aluminum Zirconium Tetrachlorohydrex Gly | 25 |
| Silicone | 40 |
| Phosphatidylglycerol | 10 |
| Emulsifier | 10 |

What is claimed is:

1. A hybrid encapsulate formulation consisting of 41% to 50% starch, 2% to 3.5% hydrocolloid, 10% to 30% sol-gel capsules, and 25% to 38% of the first fragrance, based on the dry weight of the hybrid encapsulate formulation, wherein the dry weight totals 100%; and wherein the hybrid encapsulate formulation is obtained by a method consisting essentially of (a) preparing an aqueous starch solution; (b) preparing an oil phase containing a first fragrance; (c) emulsifying the oil phase with the aqueous starch solution to obtain an emulsion; (d) mixing the emulsion with a core-shell capsule suspension to obtain a mixture, wherein the core-shell capsule suspension consists essentially of (i) prepared sol-gel capsules that encapsulate a second fragrance, and (ii) a hydrocolloid selected from the group consisting of polyvinylpyrrolidone, polyvinyl alcohol, and a combination thereof; and (e) spray drying the mixture to obtain a hybrid encapsulate formulation.

2. The hybrid encapsulate formulation of claim 1, wherein the second fragrance in the emulsion and the first fragrance in the sol-gel capsule are the same.

3. The hybrid encapsulate formulation of claim 1, wherein the second fragrance in the emulsion and the first fragrance in the sol-gel capsule are different.

4. A personal care product comprising the hybrid encapsulate formulation of claim 1.

5. The personal care product of claim 4, wherein said product is an antiperspirant or deodorant.

6. The personal care product of claim 4, wherein said product is a shampoo, hair conditioner, hair rinse, hair refresher, body wash or soap.

7. A beauty care product comprising the hybrid encapsulate formulation of claim 1.

8. The beauty care product of claim 7, wherein said product is a fine fragrance or Eau De Toilette product.

9. A fabric care product comprising the hybrid encapsulate formulation of claim 1.

10. The fabric care product of claim 9, wherein said product is a rinse conditioner, liquid detergent or powder detergent.

11. A home care product comprising the hybrid encapsulate formulation of claim 1.

12. The home care product of claim 11, wherein said product is an all-purpose cleaner or fabric refresher.

13. A personal hygiene product comprising the hybrid encapsulate formulation of claim 1.

14. The personal hygiene product of claim 13, wherein the product is a hand sanitizer.

15. An oral care product comprising the hybrid encapsulate formulation of claim 1.

16. The oral care product of claim 15, wherein the product is a tooth powder.

17. The hybrid encapsulate formulation of claim 1, wherein the hydrocolloid is polyvinylpyrrolidone.

18. The hybrid encapsulate formulation of claim 1, wherein the spray drying step is performed at a spray drying inlet temperature of 150 to 240° C.

* * * * *